United States Patent [19]

Stevenson et al.

[11] Patent Number: 5,333,095
[45] Date of Patent: Jul. 26, 1994

[54] FEEDTHROUGH FILTER CAPACITOR ASSEMBLY FOR HUMAN IMPLANT

[75] Inventors: Robert A. Stevenson, Canyon Country, Calif.; Donald N. Pruett, Carson City, Nev.

[73] Assignee: Maxwell Laboratories, Inc., Sierra Capacitor Filter Division, Carson City, Nev.

[21] Appl. No.: 55,981

[22] Filed: May 3, 1993

[51] Int. Cl.$^5$ .............................................. H01G 4/42
[52] U.S. Cl. ...................... 361/302; 29/25.42; 333/182; 333/185
[58] Field of Search ... 361/302, 306, 307, 306.1–306.3; 29/25.42; 174/143, 152 R, 152 GM; 333/182, 185

[56] References Cited

U.S. PATENT DOCUMENTS

| | | | |
|---|---|---|---|
| 2,756,375 | 7/1956 | Peck | 361/302 |
| 3,235,939 | 2/1966 | Rodriguez et al. | 29/25.42 |
| 3,920,888 | 11/1975 | Barr | 174/152 GM |
| 4,083,022 | 4/1978 | Nijman | 333/185 |
| 4,148,003 | 4/1979 | Colburn et al. | 361/302 |
| 4,152,540 | 5/1979 | Duncan et al. | 174/152 GM |
| 4,220,813 | 9/1980 | Kyle | 174/152 GM |
| 4,247,881 | 1/1981 | Coleman | 361/302 |
| 4,314,213 | 2/1982 | Wakino | 361/302 |
| 4,352,951 | 10/1982 | Kyle | 174/152 GM |
| 4,362,792 | 12/1982 | Bowsky et al. | 174/152 GM |
| 4,421,947 | 12/1983 | Kyle | 174/152 GM |
| 4,424,551 | 1/1984 | Stevenson et al. | 361/302 |
| 4,456,786 | 6/1984 | Kyle | 174/152 GM |
| 4,737,601 | 4/1988 | Gartzke | 174/152 GM |
| 4,741,710 | 5/1988 | Hogan et al. | 333/185 |
| 5,032,692 | 7/1991 | DeVolder | 361/30.2 |
| 5,070,605 | 12/1991 | Daglow et al. | 29/842 |

Primary Examiner—Bruce A. Reynolds
Assistant Examiner—Gregory L. Mills
Attorney, Agent, or Firm—Kelly Bauersfeld & Lowry

[57] ABSTRACT

A feedthrough filter capacitor assembly and related installation method are provided for shielding a conductive terminal pin or lead of the type used, for example, in an implantable medical device such as a heart pacemaker or defibrillator, against passage of external interference signals. The feedthrough assembly includes a terminal pin subassembly having at least one terminal pin supported within a cylindrical conductive ferrule by a hermetically sealed insulator ring. The ferrule is adapted for mounting onto a conductive pacemaker housing, as by welding or brazing, to support the terminal pin for feedthrough passage to the housing interior. A co-axial filter capacitor is mounted at an inboard side of the pacemaker housing, with capacitor electrode plate sets coupled respectively to the pacemaker housing and to the terminal pin by a conductive adhesive or the like. In one preferred form, multiple filter capacitors are provided in a substantially coplanar array within a common base structure, with each capacitor in association with a respective terminal pin.

21 Claims, 6 Drawing Sheets

FEEDTHROUGH FILTER CAPACITOR ASSEMBLY FOR HUMAN IMPLANT

BACKGROUND OF THE INVENTION

This invention relates generally to improvements in feedthrough terminal pin assemblies and related methods of installation, particularly of the type used in implantable medical devices such as heart pacemakers and the like to decouple undesired interference signals from the device. More specifically, this invention relates to an improved feedthrough terminal pin and capacitor assembly and related installation method, including one or more filter capacitors, and adapted particularly for use in connecting a lead wire or electrode through a hermetically sealed housing to internal electronic components of the medical device while decoupling interference signals against entry into the sealed housing. The invention is particularly designed for use in heart pacemakers (bradycardia), defibrillators (tachycardia), and combined pacemaker defibrillator devices.

Feedthrough terminal pin assemblies are generally known in the art for connecting electrical signals through the housing or case of an electronic instrument. For example, in implantable medical devices especially such as a heart pacemaker or defibrillator or the like, the terminal pin assembly comprises one or more conductive terminal pins supported by an insulator structure for feedthrough passage from the exterior to the interior of the medical device. Many different insulator structures and related mounting methods are known in the art for use in medical devices wherein the insulator structure also provides a hermetic seal to prevent entry of body fluids into the housing of the medical device. However, the feedthrough terminal pins are connected to one or more lead wires which effectively act as an antenna and thus tend to collect stray or electromagnetic interference (EMI) signals for transmission to the interior of the medical device. In some prior art devices, the medical device has included ceramic chip capacitors which have been added to the internal electronics of the device in an effort to filter and thus control the effects of such interference signals. This internal, so-called "on-board" filtering technique has potentially serious disadvantages due to intrinsic parasitic resonances of the chip capacitors, in combination with permitting EMI entry into the interior of the device housing. In another and normally preferred approach, a filter capacitor has been combined directly with the terminal pin assembly to decouple interference signals to the housing of the medical device.

In a typical construction, a coaxial feedthrough filter capacitor used in a feedthrough assembly to suppress and decouple undesired interference or noise transmission along a terminal pin comprises a so-called discoidal capacitor having two sets of electrode plates embedded in spaced relation within an insulative substrate or base, formed typically as a ceramic monolith. One set of the electrode plates is electrically connected at an inner diameter surface of the discoidal structure to the conductive terminal pin utilized to pass the desired electrical signal or signals. The other or second set of electrode plates is coupled at an outer diameter surface of the discoidal capacitor to a cylindrical ferrule of conductive material, wherein the ferrule is electrically connected in turn to the conductive housing or case of the electronic instrument. In operation, the discoidal capacitor permits passage of relatively low frequency electrical signals along the terminal pin, while shunting and shielding undesired interference signals of typically high frequency to the conductive housing. Feedthrough capacitors of this general type are commonly employed in implantable heart pacemakers and defibrillators and the like, wherein the pacemaker housing is constructed from a conductive biocompatible metal, such as titanium alloy which is electrically coupled to the feedthrough filter capacitor. As a result, the filter capacitor and terminal pin assembly prevents entry of interference signals to the interior of the pacemaker housing, wherein such interference signals could otherwise adversely affect the desired heart pacing of defibrillating function.

In the past, feedthrough filter capacitors for heart pacemakers and the like have typically been constructed by preassembly of the discoidal capacitor with a terminal pin subassembly which includes the conductive terminal pin and ferrule. More specifically, the terminal pin subassembly is prefabricated to include one or more conductive terminal pins supported within the conductive ferrule by means of a hermetically sealed insulator ring or bead. See, for example, the terminal pin subassemblies disclosed in U.S. Pat. Nos. 3,920,888; 4,152,540; 4,421,947; and 4,424,5511. The terminal pin subassembly thus defines a small annular space or gap disposed radially between the inner terminal pin and the outer ferrule. A small discoidal capacitor of appropriate size and shape is then installed into this annular space or gap, in conductive relation with the terminal pin and ferrule, by means of soldering, conductive adhesive, etc. The thus-constructed feedthrough capacitor assembly is then mounted within an opening in the pacemaker housing, with the conductive ferrule in electrical and hermetically sealed relation with the housing of the medical device.

Although feedthrough filter capacitor assemblies of the type described above have performed in a generally satisfactory manner, the manufacture and installation of such filter capacitor assemblies has been relatively costly and difficult. For example, installation of the discoidal capacitor into the small annular space between the terminal pin and ferrule can be a difficult and complex multi-step procedure to ensure formation of reliable, high quality electrical connections. Moreover, installation of the capacitor at this location inherently limits the capacitor to a small size and thus also limits the capacitance thereof. Similarly, subsequent attachment of the conductive ferrule to the pacemaker housing, typically by welding or brazing processes or the like, can expose the fragile ceramic discoidal capacitor to temperature variations sufficient to create the risk of capacitor cracking and failure.

There exists, therefore, a significant need for improvements in feedthrough filter capacitor assemblies of the type used, for example, in implantable medical devices such as heart pacemakers and the like, wherein the filter capacitor is designed for relatively simplified and economical, yet highly reliable installation with respect to a conductive terminal pin and associated conductive pacemaker housing or shield. In addition, there exists a need for an improved feedthrough assembly having a discoidal capacitor which can be designed to provide a significantly increased capacitance for improved filtering. The present invention fulfills these needs and provides further related advantages.

SUMMARY OF THE INVENTION

In accordance with the invention, an improved feedthrough filter capacitor assembly is provided for shielding or filtering undesired interference signals from a conductive terminal pin or lead, particularly of the type used in an implantable medical device such as a heart pacemaker or the like. The feedthrough assembly comprises a filter capacitor adapted for mounting at one side of a terminal pin subassembly in coaxial and operative relation with an associated terminal pin. In the preferred form, the terminal pin subassembly is prefabricated and p rein stalled onto a conductive substrate shield, such as the conductive housing of a heart pacemaker. The filter capacitor is then assembled quickly and easily onto the pacemaker housing, or alternately onto the terminal pin subassembly, in surrounding and operative relation with the terminal pin subassembly. A counterbore may be formed in one side of the filter capacitor to facilitate and permit close-fitting component assembly. In another preferred form, the terminal pin subassembly and the capacitor are mounted onto a conductive subplate which is then mounted in turn to the conductive housing of the medical device.

The terminal pin subassembly comprises a prefabricated unit including at least one conductive pin or lead supported within a cylindrical conductive ferrule by means of a hermetically sealed insulator ring. The ferrule is then mounted in hermetically sealed and electrically conductive relation within an opening in the pacemaker housing by means of welding or brazing or the like. In this configuration, the ferrule is mounted directly on the pacemaker housing in electrically conductive relation with the pacemaker housing, whereas the terminal pin provides a conductive lead extending in hermetically sealed and electrically insulted relation between the exterior and interior of the pacemaker housing.

A discoidal-type filter capacitor is mounted onto the pacemaker housing, preferably at an inboard surface thereof, with the conductive ferrule disposed within the capacitor counterbore. The filter capacitor includes a relatively small central opening for pass-through reception of the terminal pin. A first set of capacitor electrode plates is connected electrically to the central capacitor opening, as by metallization of the inner diameter surface thereof. A second set of capacitor electrode plates is electrically connected with an exterior capacitor surface, as by metallization of at least a portion of the capacitor exterior. The capacitor is mounted quickly and easily, preferably by means of a conductive adhesive or soldering or the like, for electrically connecting the capacitor electrode plate sets respectively to the terminal pin and to the pacemaker housing, in hermetically sealed relation therewith. A shallow counterbore is formed in one side of the discoidal capacitor, in accordance one preferred embodiment of the invention, to accommodate the ferrule which may protrude inwardly a short distance from the pacemaker housing. In another embodiment, the ferrule is formed to be substantially flush with an inboard surface of the housing, wherein the counterbore in the capacitor may be omitted. In still another embodiment, the ferrule and capacitor are assembled on a conductive subplate which is adapted in turn to mount onto the housing of the medical device.

In an alternative preferred form of the invention, a plurality of filter capacitors may be formed in substantially coplanar array within a common base structure. The size and shape of the capacitor base structure, in combination with the positions of any counterbore formed therein, are provided for mounting of the base structure in a single step over a corresponding plurality of terminal pin subassemblies preinstalled onto a pacemaker housing.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is a diagrammatic illustration depicting a heart pacemaker implanted within the body of a patient;

FIG. 2 is an enlarged fragmented sectional view illustrating a feedthrough filter capacitor assembly embodying the novel features of the invention;

FIG. 3 is a fragmented vertical sectional view of a terminal pin subassembly for use in the invention;

FIG. 4 is a fragmented sectional view similar to FIG. 3, and illustrating mounting of the terminal pin subasemby onto the conductive housing of a heart pacemaker or the like;

DETAILED DESCRIPTION OF THE PREFERRED EMBODIMENTS

Figures 1, 2, 3, 4:
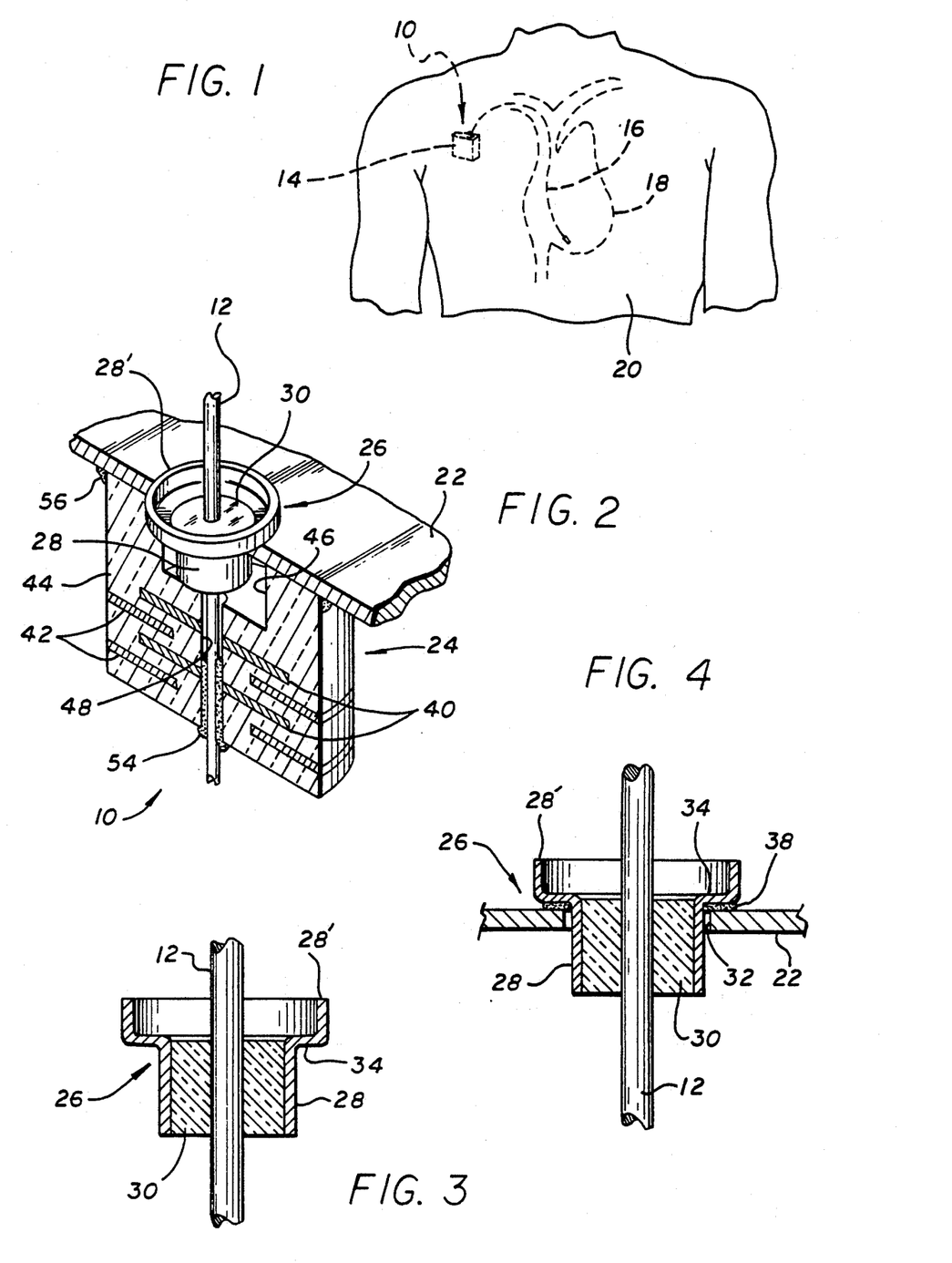

As shown in the exemplary drawings, a feedthrough capacitor assembly referred to generally in FIG. 2 by the reference numeral 10 is provided for suppressing or filtering and shielding undesired electrical interference signals from a conductive terminal pin or lead 12. As shown in FIG. 1, the feedthrough assembly 10 is particularly adapted for use in an implantable medical device such as a heart pacemaker or defibrillator 14 or the like for supplying electrical signals via a lead 16 to the heart 18 of a patient 20. The feedthrough assembly 10 is designed for simplified installation onto a conductive housing 22 (FIG. 2) of the medical device 14 to provide a hermetically sealed electrical connection to the conductive lead 16 through the housing 22 for appropriate connection to electronic components (not shown) within the medical device, while attenuating and shielding unwanted interference signals along the lead 12 and thereby preventing significant transmission of said signals into the interior of the housing.

Figures 5, 6, 7, 8:
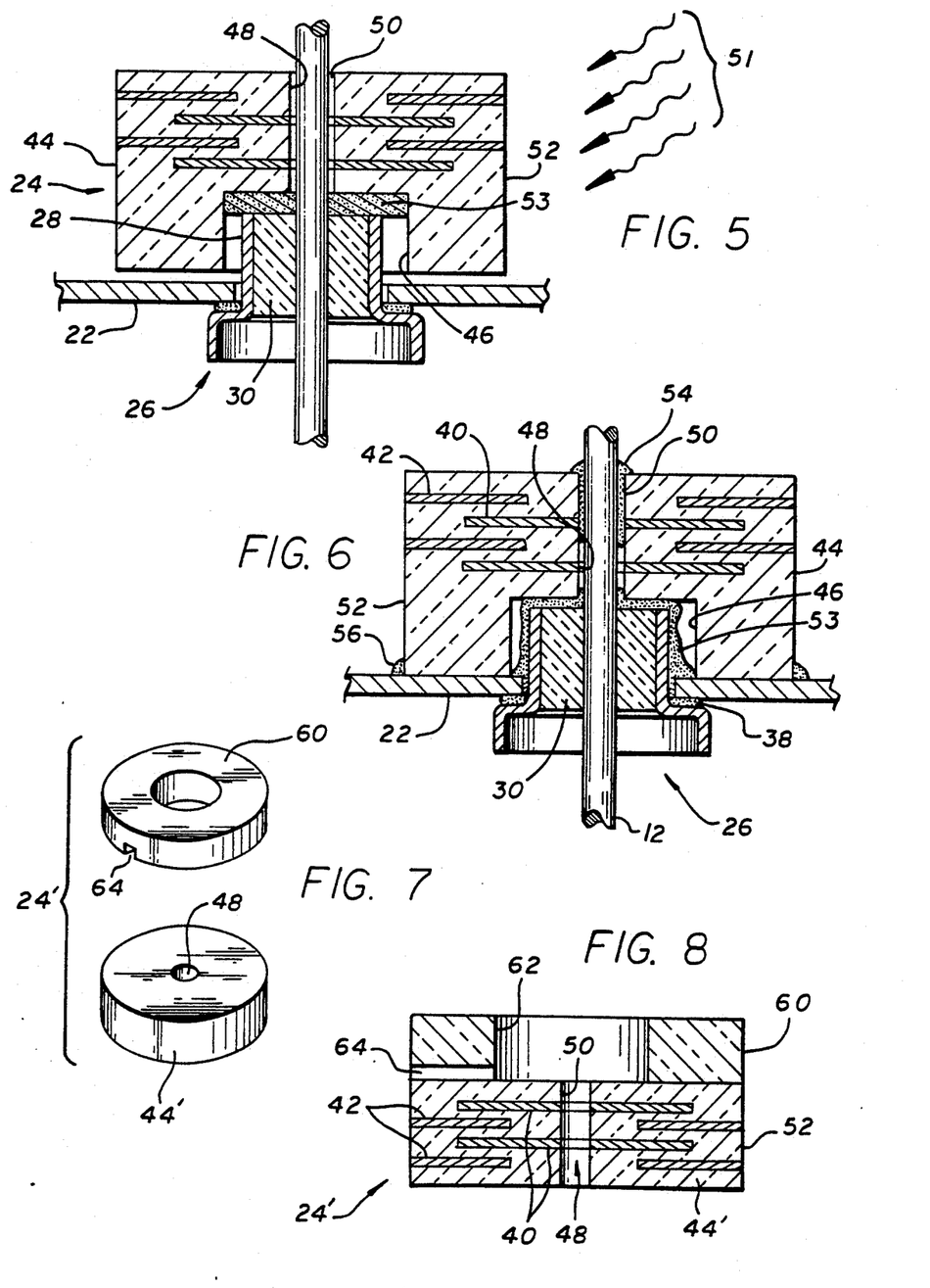
FIG. 5 is a fragmented and inverted vertical sectional view similar to FIG. 4, and illustrating mounting of a filter capacitor in a position over the terminal pin subassembly, at one side of the heart pacemaker housing.
FIG. 6 is a fragmented vertical sectional view similar to FIG. 5, and showing conductive attachment of the filter capacitor to a terminal pin and to the pacemaker housing.
FIG. 7 is an exploded perspective view illustrating one alternative preferred form for the filter capacitor for use in the invention.
FIG. 8 is an enlarged vertical sectional view illustrating the filter capacitor of FIG. 7, in assembled form.

In general terms, as viewed in FIGS. 2 and 5, the feedthrough filter capacitor assembly 10 of the present invention includes a feedthrough filter capacitor 24 in combination with a terminal pin subassembly 26 which can be constructed separately from the capacitor as a prefabricated unit, or otherwise obtained as an available commercial product. The filter capacitor 24 and terminal pin subassembly 26 are desirably mounted separately onto the pacemaker housing 22, with the capacitor 24 generally surrounding and preferably overlying the terminal pin subassembly 26. In some embodiments, the capacitor may be mounted directly to the terminal pin subassembly, before or after attachment thereof to the housing 22. With these configurations, as will be described in more detail, the components of the feedthrough assembly 10 can be constructed and installed in a cost-efficient and reliable manner, while providing the terminal pin 12 with effective attenuation and shielding against passage of unwanted noise signals.

The terminal pin subassembly 26 is shown best in FIGS. 3 and 4 to include the conductive lead 12 formed typically from a selected and biocompatible metal, such as platinum, tantalum or niobium wire or the like. The conductive lead or pin 12 is provided, as is known in the art, for passage of electrical signals through the housing 22, with one or more such conductive pins 12 being required in a typical pacemaker or defibrillator applicator in accordance with the number of leads 16. The conductive pin 12 is adapted for electrical connection (not shown) to the associated lead 16, and further to electronic control circuitry (also not shown) within the pacemaker housing of the medical device, as known to persons skilled in the art.

As shown in FIG. 3, the terminal pin 12 is supported within an outer cylindrical ferrule 28 formed from a suitable conductive material, such as titanium or titanium alloy. The terminal pin 12 is supported within the ferrule 28 in spaced nonconductive relation, by means of an insulative mounting ring or bead 30. This insulator ring 30 provides a hermetic seal to prevent passage of body fluids through the terminal pin subassembly 26, when said subassembly is mounted onto the pacemaker housing 22. Glass-fired or ceramic-based materials such as polycrystaline alumina, sapphire crystal or the like are commonly used to form the insulator ring 30. Examples of prefabricated terminal pin subassemblies of this general type are shown and described in more detail in U.S. Pat. Nos. 3,920,885 and 4,421,947 which are incorporated by reference herein.

As shown in FIG. 4, in accordance with the apparatus and method of the present invention, the prefabricated terminal pin subassembly 26 is adapted for quick and easy mounting onto the housing 22, within a preformed opening 32 formed therein. In this regard, the preferred ferrule shape includes an outboard end segment 28' of expanded diametric size to define a radially outwardly projecting shoulder 34 sized to seat against an outboard surface of the housing 22, with the smaller diameter inboard end of the ferrule 28 projecting axially through the opening 32 to the interior of the pacemaker housing. The ferrule 28 is securely connected to the conductive housing 22, formed typically from titanium or titanium alloy, by means of a welded or brazed connection 38. Importantly, this connection 38 forms a high quality electrical connection between the ferrule 28 and the housing 22, while additionally providing a hermetic seal therebetween. The terminal pin 12 is thus supported on the housing 22, in hermetically sealed and electrically insulated relation, for passage through the housing opening 32.

The filter capacitor 24 comprises, in the form shown in FIGS. 2, 5 and 6, a discoidal capacitor having first and second sets of electrode plates 40 and 42 embedded within an insulative or dielectric base structure 44 of ceramic monolith construction or the like. Although the exemplary drawings show in exaggerated scale a pair of conductive plates 40 in parallel staggered relation with a corresponding pair of the conductive plates 42, it will be understood that a large plurality of typically 5-40 conductive plates 40 will be provided in alternatingly stacked and parallel spaced relation with a corresponding number of the plates 42. One side of the illustrative discoidal capacitor defines a counterbore 46 having a sufficient radial size and axial depth to permit placement of the capacitor 24 in seated relation against the inboard surface of the housing 22, with the inboard-extending portion of the ferrule 28 received within the capacitor counterbore 46. In this configuration, the terminal pin 12 projects through a central opening 48 in the capacitor 24, wherein this central opening 48 is coaxially aligned with the counterbore 46.

The set of inner electrode plates 40 include marginal edges communicating with the inner diameter surface of the discoidal capacitor 24, at the central opening 48. As known in the art, this central opening is normally lined with a metallized or silverized or plated metallic film for electrically connecting the plates 40 to each other. Similarly, the second or outer set of the electrode plates 42 include outer margins disposed at the periphery of the capacitor base structure 44, wherein these outer plates 42 are electrically connected to each other by an appropriate metallized or silverized or plated metallic film. These metallized films at the inner and outer surfaces of the capacitor 24 are identified in FIGS. 5 and 6 by the reference numerals 50 and 52, respectively.

FIGS. 5 and 6 depict a preferred method of constructing the feedthrough capacitor assembly 10, wherein the filter capacitor 24 is placed over the inverted terminal pin subassembly 26. An optional diskshaped epoxy preform 53 (FIG. 5) can be positioned about the terminal pin 12 at a location sandwiched between the inboard-extending end of the ferrule 28 and the bottom of the capacitor counterbore 46. In this position, the epoxy preform 53 supports the capacitor 24 in slight spaced relation above the inboard face of the housing 22. The partially assembled structure as described is placed in an oven and subjected to heat represented by arrows 51 in an amount sufficient to cause the epoxy preform 53 to melt and flow. As the melting of the preform occurs, a portion of the epoxy is drawn into the adjacent end of the capacitor opening 48 to close and seal that opening at the counterbore 46 (FIG. 6). Additional epoxy flows down around the ferrule 28, concurrently with downward movement of the capacitor 24 to a position seated flush on the housing 22. Sufficient epoxy flows to the juncture of the housing 22 and the counterbore periphery to secure or fixture the capacitor onto the housing 22, when the epoxy cures to a rigid state.

The metallized surface 50 within the central capacitor opening 48 is then connected electrically to the terminal pin 12 by means of a conductive adhesive bead 54, or by soldering or brazing or the like. In the preferred form, the conductive adhesive 54 is applied to the annular gap between the pin 12 and the capacitor surface 50, and allowed to fill a portion (about one-half) of the gap length. Similarly, the metallized surface 52 associated with the outer electrode plates 42 of the capacitor is connected electrically to the inboard surface of the pacemaker housing 22 by means of an additional fillet 56 of conductive adhesive or the like. One preferred conductive adhesive comprises a curable polyimide adhesive loaded with conductive particles such as spheres or flakes, as described by way of example in U.S. Pat. No. 4,424,551, which is incorporated by reference herein. However, it will be understood that other conductive connecting means may be used, such as solder, braze or the like. Importantly, the adhesive beads 54, 56 establish an electrically conductive mounting of the capacitor 24 in a secured stable manner to the housing 22.

In use, the thus-installed capacitor 24 effectively decouples and shields unwanted noise signals from the conductive lead 12, by capacitively connecting those signals to the housing 22. That is, the housing 22 cooperates with the capacitor 24 and the terminal 26 to form an integral shield which reflects and absorbs the undesired radiated noise signals and thereby prevents entry of those signals into the interior of the housing. Installation of the capacitor 24 in association with the terminal pin subassembly 26, in overlying and surrounding relation therewith, is significantly easier than conventional capacitor installation into the small annular gap formed radially between the conductive pin 12 and ferrule 28 of the terminal pin subassembly. In addition, the diametric size of the capacitor is not restricted to the size of the small annular gap, whereby a filter capacitor of significantly increased capacitance for improved filter efficiency can be used. Moreover, mounting of the capacitor 24 subsequent to welded or brazed connection of the terminal pin subassembly 26 to the housing 22 avoids exposure of the ceramic capacitor structure to high welding temperatures.

One alternative preferred form of a feedthrough discoidal filter capacitor for use in the present invention is shown in FIGS. 7 and 8, wherein a modified filter capacitor 24' is formed by assembly of a primary base structure 44' with a mounting ring 60. More specifically, the capacitor base structure 44' comprises a conventional discoidal capacitor having the sets of conductive plates 40 and 42 embedded therein. This discoidal capacitor can be produced according to conventional techniques to include the relatively small central opening 48. The mounting ring 60 is formed from a structure which corresponds to or is otherwise compatible with the capacitor base structure 44', to include a conforming outer peripheral shape in combination with a central opening 62 which is much larger than the opening 48. These two components 44' and 60' are connected together in coaxial relation by suitable bonding as viewed in FIG. 7. These components can be formed from similar ceramic material and bonded together in the unfired or green state followed by co-firing to form a single monolith structure. Alternately, the components can be individually fired and thereafter bonded by glass frit at approximately 600° C., nonconductive polyimide at about 270° C., or epoxies at about 150° C. The central opening 48 and the peripheries of both components 44', 60 are then metallized with the film surfaces 50 and 52, as previously described. The assembled components cooperatively define the counterbore 46 for receiving the ferrule 28 of a terminal pin subassembly, as previously described. A radially open vent or notch 64 may be formed in the mounting ring 60 to accommodate vented passage of outgas constituents in the course of curing conductive adhesive materials. The metallized surface 52 is continued on the exterior of the mounting ring 60 for electrical connection to the housing 22, all in accordance with the method of assembly as previously described.

Figure 9:
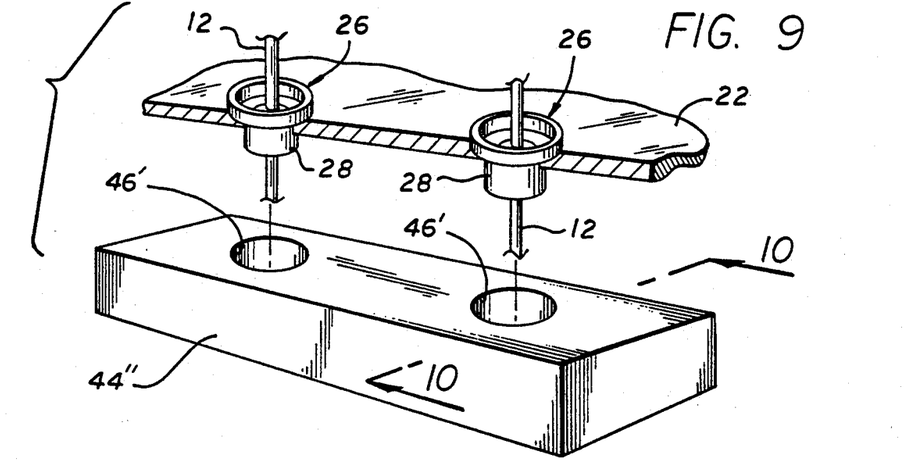
FIG. 9 is a fragmented exploded perspective view illustrating another alternative preferred form of the invention.
Figure 10:
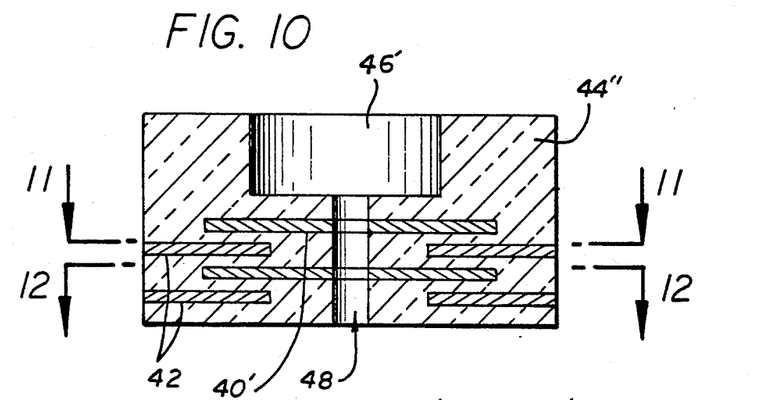
FIG. 10 is an enlarged vertical sectional view taken generally on the line 10—10 of FIG. 9.
Figure 11:
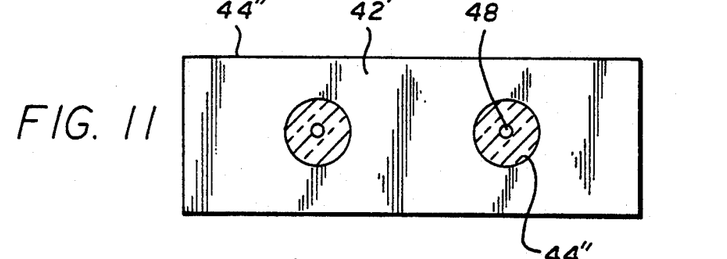
FIG. 11 is an enlarged horizontal sectional view taken generally on the line 11—11 of FIG. 10.
Figure 12:
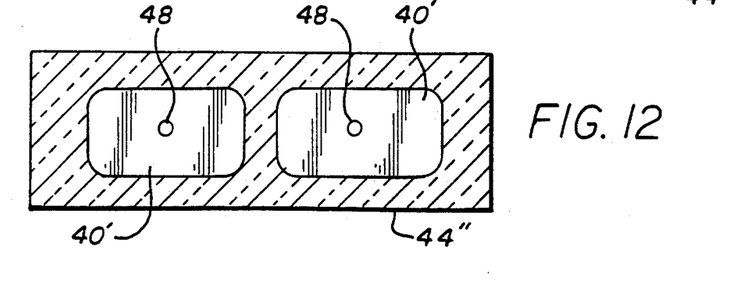
FIG. 12 is an enlarged horizontal sectional view taken generally on the line 12—12 of FIG. 10.
Figure 13:
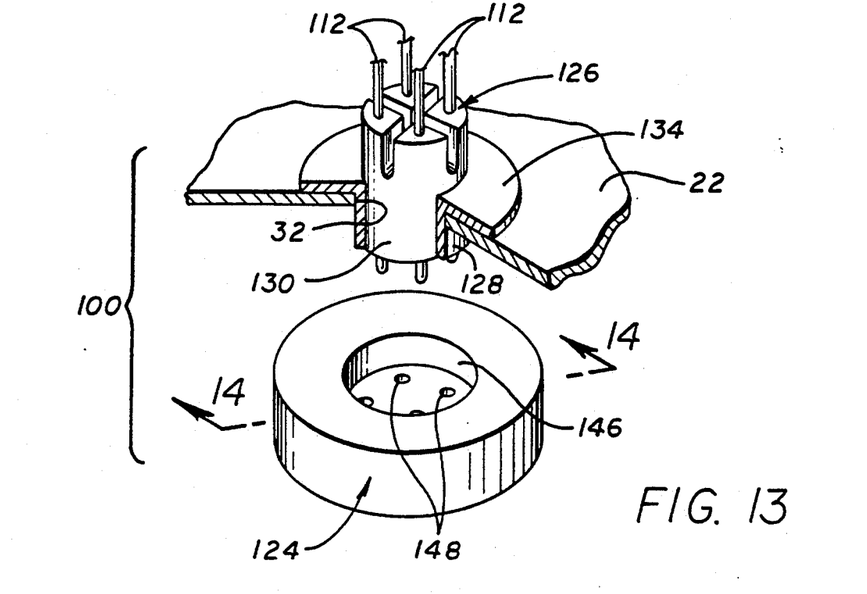
FIG. 13 is an exploded and fragmented perspective view showing another alternative preferred form of the invention.

FIGS. 9-12 illustrate another alternative preferred form of the invention, wherein a further modified capacitor base structure 44'' includes a plurality of feedthrough filter capacitors disposed in a unitized and substantially planar array with each filter capacitor defined by sets of embedded electrode plates 40' and 42'. In this configuration, each filter capacitor is associated with a corresponding counterbore 46' for mounting over the ferrule 28 of a corresponding terminal pin subassembly 26. The multicapacitor base structure 44'' can be constructed as a monolithic base in the manner described with respect to FIGS. 2, 5 and 6, or in the form of assembled base components as described with respect to FIGS. 7 and 8. Moreover, as viewed in FIG. 11, the outer ground electrode plates 42' for the multiple filter capacitors may be common plates. In a medical device 14 having multiple conductive leads 12, the single capacitor structure 44'' having the multiple coplanar filter capacitors therein may be installed onto the inboard side of the housing 22 in a single step, by installing the monolithic capacitor base structure over several terminal pin subassemblies 26 (FIG. 9). Once again, the outer grounding electrodes 42' can be connected to the housing 22 by means of conductive adhesive or the like, with the terminal pin 12 of each terminal pin subassembly 26 also connected quickly and easily to the associated capacitor by means of conductive adhesive.

FIGS. 13-16 show another alternative form of the invention, wherein a modified feedthrough filter capacitor assembly 100 is formed by a combination of a feedthrough filter capacitor 124 with a conventional and commercially available multiconductor terminal pin subassembly 126. The illustrative terminal pin subassembly has four parallel terminal pins 112 supported in insulative relation within a typically glass-based or ceramic based insulator ring 130 mounted in turn within a cylindrical conductive ferrule 128. The ferrule 128 includes a radially outwardly projecting flange 134 for secure attachment in a hermetically sealed manner, as by welding or brazing, to a conductive housing 22 of an implanted medical device or the like. The ferrule flange 134 supports the ferrule 128 with quad-mounted terminal pins 112 extending through an opening 32 in the housing.

Figure 14:
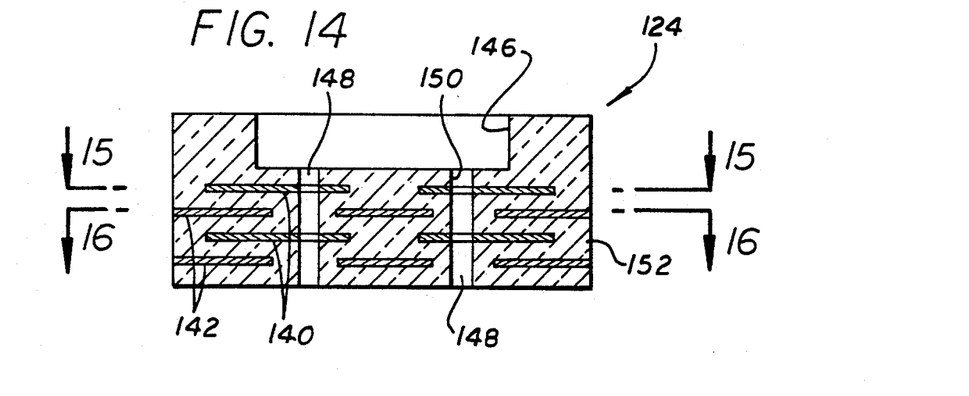
FIG. 14 is an enlarged vertical sectional view taken generally on the line 14—14 of FIG. 13.
Figure 15:
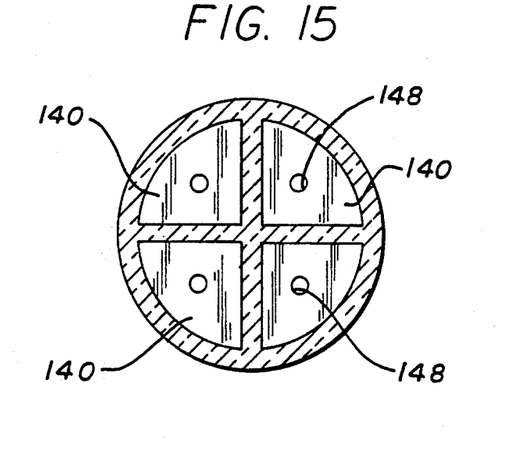
FIG. 15 is a horizontal sectional view taken generally on the line 15—15 of FIG. 14.
Figure 16:
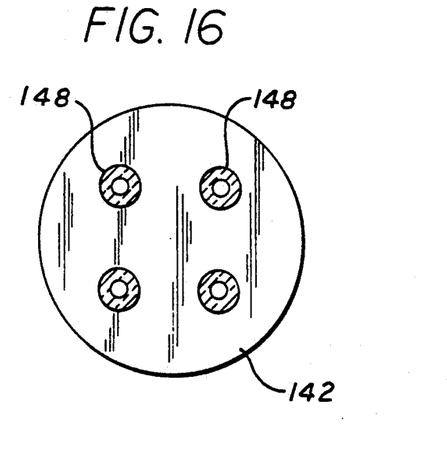
FIG. 16 is a horizontal sectional view taken generally on the line 16—16 of FIG. 14.

Subsequent to mounting of the terminal pin subassembly 126, as described, the capacitor 124 is mounted onto the inboard side or face of the housing 22. The illustrative capacitor 124 includes a counterbore 146 in one side thereof to accommodate the inboard-projecting portions of the terminal pin subassembly 126. A series of four openings 148 are formed in the capacitor 124 for through passage of the four terminal pins 112. As shown in FIGS. 14–16, the capacitor openings 148 are individually associated with pie-shaped inner conductive electrode plates 140 stacked in alternate array with commonly formed ground electrode plates 142. The inner plates are electrically connected at the associated opening 148, by a metallized surface film 150, and the ground plates are electrically connected at the capacitor periphery to a metallized surface film 152. The capacitor 124 is mounted onto the housing 22, in respective electrical connection with the housing 22 and the multiple terminal pins 112 in the same manner as described previously with respect to FIGS. 1 through 12.

Figures 17, 18:
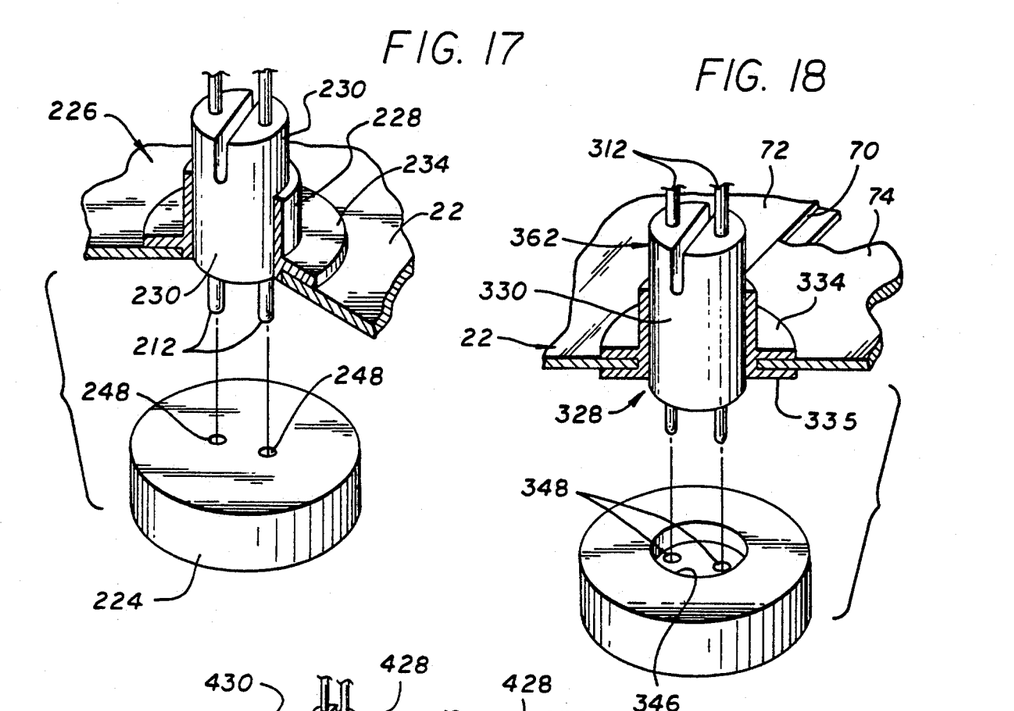
FIG. 17 is an exploded and fragmented perspective view depicting a further alternative preferred embodiment of the invention.
FIG. 18 is another exploded and fragmented perspective view of an alternative preferred form of the invention.

Another alternative embodiment is shown in FIG. 17, wherein a flush-mounted feedthrough filter capacitor 224 is provided for installation at the inboard face of a conductive housing 22 or the like in operative association with a terminal pin subassembly 226. In this configuration, the terminal pin subassembly includes a ferrule 228 mounted by an outer flange 234 to the housing 22, with an insulator ring 230 contained within the ferrule and supporting a pair of feedthrough terminal pins 212. The ferrule 228 and insulator ring 230 are designed to define a flush surface which does not protrude beyond the inboard face of the housing 22 into the housing interior. The capacitor 224, shown with a pair of openings 248 for through passage of the terminal pins 212 may thus omit the counterbore described with respect to other embodiments of the invention. Importantly, however, the capacitor 224 is mounted in operative association with the terminal pins 212 in the same manner as previously described, subsequent to mounting of the terminal pin subassembly onto the housing 22. Appropriate sets of conductive plates are contained within the capacitor 224 to provide the desired signal filtering and shielding function.

FIG. 18 depicts another modified assembly adapted for convenient installation along a seam 70 defined upon assemblage of conductive shells 72 and 74 which cooperatively define the housing 22 of the pacemaker or the like. In this version of the invention, a terminal pin subassembly 362 includes a modified ferrule 328 having the insulator ring 330 and associated terminal pin or pins 312 supported therein. The modified ferrule 328 is adapted for assembly with a feedthrough filter capacitor 324, which may correspond with the capacitor 224 of FIG. 17 modified to include a counterbore 346 surrounding the terminal pin openings 348.

The ferrule 328 of FIG. 18 includes outboard and inboard flanges 334 and 335 spaced apart sufficient to define an outwardly open circumferential groove to receive adjacent edges of the housing shells 72 and 74. The ferrule 328 is preassembled first to one of the housing shells 72 or 74, followed by appropriate mounting of the capacitor 324 to the inboard flange 335. In this regard, the inboard flange has a sufficient radial size for capacitor mounting thereto in the same manner as previously described with respect to mounting of the feedthrough capacitor directly to the housing. The other housing shell is then fitted with the ferrule to close the housing 22, and a hermetic seal can be formed as by welding the periphery of the outboard flange 334 to the housing. The seam 70 is also closed in the same manner to provide a hermetic seal.

Figure 19:
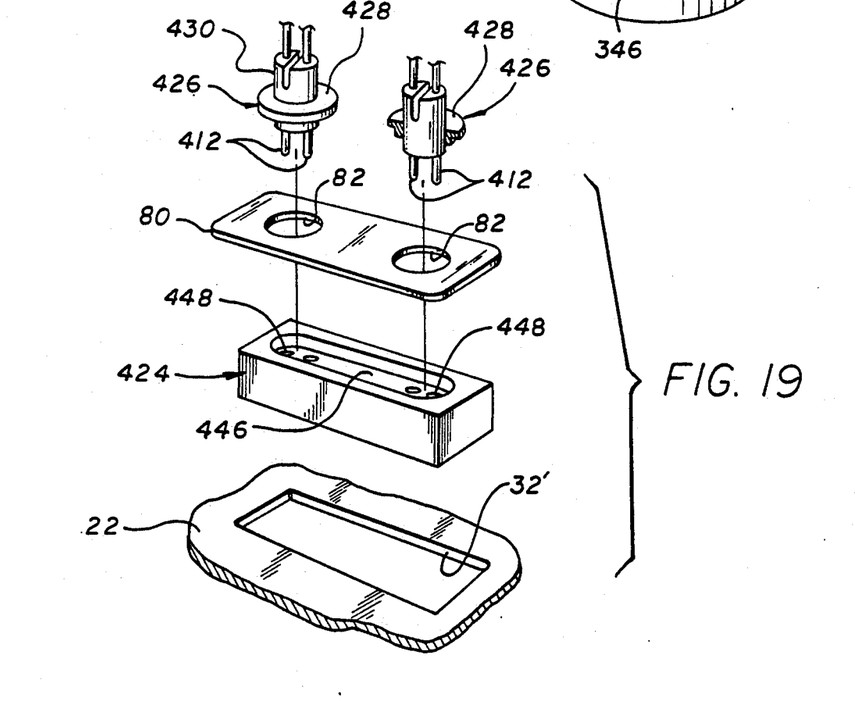
FIG. 19 is an exploded and fragmented perspective view of still another alternative preferred embodiment of the invention.

FIG. 19 shows another multicapacitor embodiment wherein an elongated micro-planar array feedthrough capacitor 424 including internal conductive plate sets (not shown) is adapted for mounting onto the inboard side of a pacemaker housing 22 or the like. The capacitor 424 is shown with two pairs of through openings 448 disposed to receive terminal pins 412 of a pair of bipolar terminal pin subassemblies 426. Each terminal pin subassembly 426 includes an insulator ring 430 to support the associated pair of terminal pins within a conductive outer ferrule 428 shown with a shape generally corresponding with the ferrule 128 of FIG. 13. The ferrules 428 are adapted for mounting as by welding or brazing onto a subplate 80 of conductive metal having openings 82 therein. The capacitor 424 is then mounted onto the inboard side of the subplate 80, in operative relation with the terminal pins 412, in the same manner as previously described. The subplate 80 is thereafter mounted over an elongated opening 32' in the housing 22 by welding or soldering. As elongated counterbore 446 is formed as by machining into one side of the capacitor base to accommodate inboard—extending portions of the terminal pin assemblies. In this embodiment, a rectangular feedthrough capacitor structure is shown in relation to the pair of terminal pin subassemblies of circular cross-sectional shape.

Figure 20:
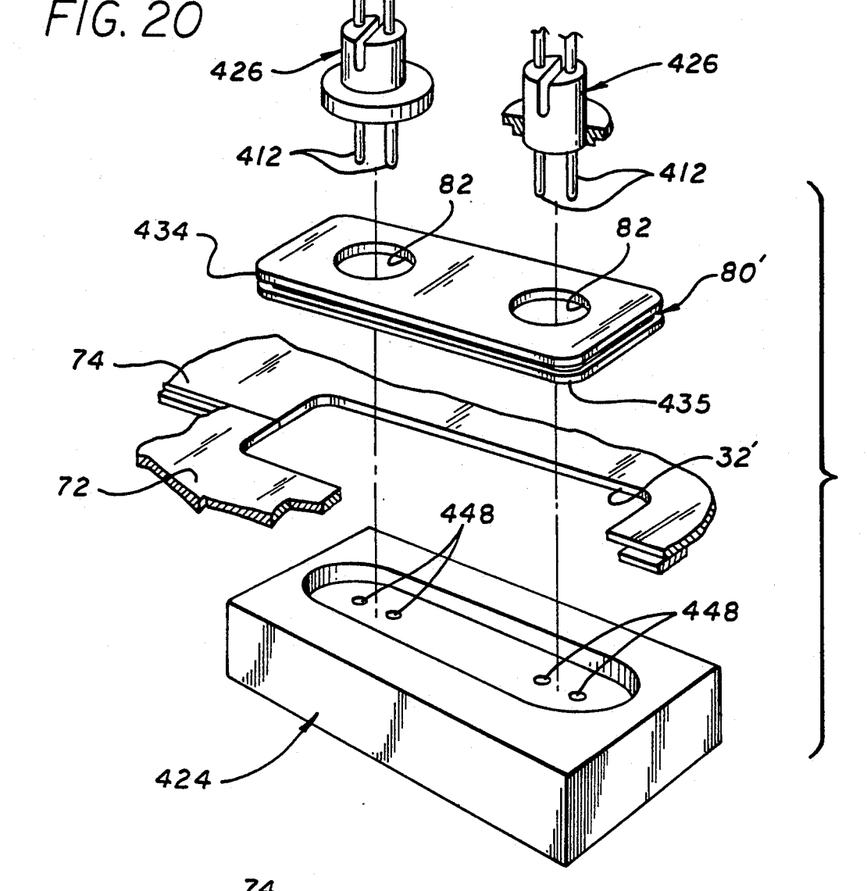
FIG. 20 is an exploded perspective view similar to FIG. 19, and illustrating a modified form of the invention.

A modified multicapacitor embodiment is shown in FIG. 20, wherein structural components corresponding with those depicted in FIG. 19 are identified by the same reference numerals. As shown, a pair of bipolar terminal pin subassemblies 426 having terminal pins 412 are mounted onto a modified subplate 80', to extend through openings 82 in the subplate. The modified subplate 80' includes upper and lower, outwardly radiating flanges 434 and 435 defining a circumferential groove. The subplate 80' is adapted in turn for installation within the housing opening 32', defined by aligned half-openings formed in adjacent interfitting housing shells 72 and 74 of the type shown previously in FIG. 18. The subplate 80', with terminal pin subassemblies 426 thereon, is assembled first to one of the housing shells 72 or 74, followed by mounting of the multiconductor capacitor 424 onto the inboard flange 435, and follow-on assembly of the other housing shell within subplate groove. Alternately, the capacitor 424 can be assembled to the inboard flange of the subplate 80' with terminal pin subassemblies pre-installed thereon, followed by installation of the housing shells with the subplate groove.

Figure 21:
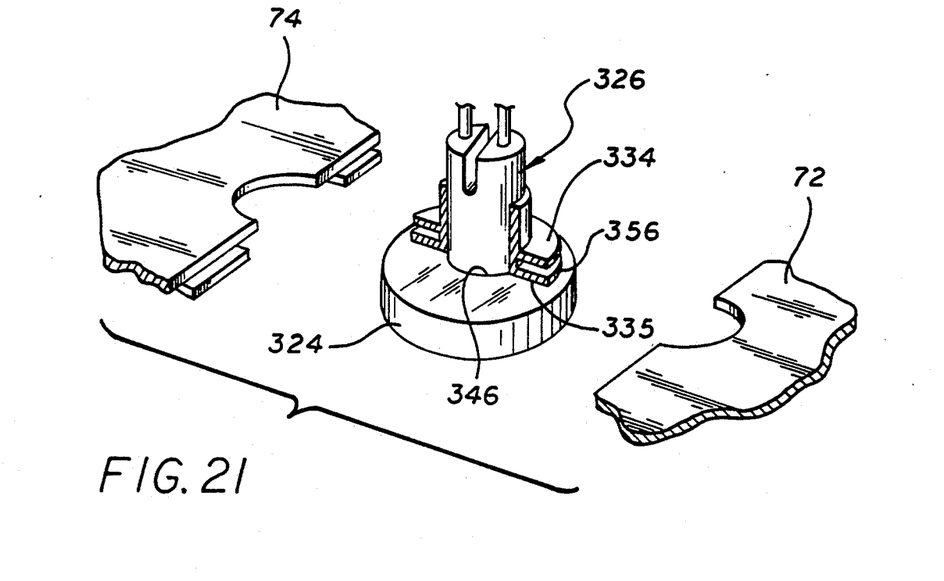
FIG. 21 is a fragmented exploded perspective view showing a still further alternative form of the invention.

Mounting of a feedthrough capacitor onto a terminal pin subassembly prior to installation onto the housing is shown in more detail in FIG. 21, wherein a bipolar terminal pin subassembly 326 and associated feedthrough capacitor 324 are provided of the type depicted previously in FIG. 18. In this version, the pre-constructed terminal pin subassembly 326 is mounted on the feedthrough capacitor 324, preferably by means of an annular bead 356 of conductive adhesive or the like applied to the capacitor at the periphery of the inboard ferrule flange 335. This resultant feedthrough assembly is then installed onto one of the associated housing shells 72 or 74, with the recess edge of the housing shell fitted into the groove defined between the ferrule flanges 334, 335. Electrical connections to the terminal pins of the medical device can then be completed, followed by assembly with the other housing shell to close and seal the housing.

The improved feedthrough capacitor assembly of the present invention may thus be implemented in a variety of specific configurations to provide a simplified and economical assembly of a feedthrough filter capacitor with a prefabricated terminal pin subassembly. In view of the embodiments as shown and described, it will be understood that features of the disclosed forms may be interchanged to provide a terminal pin subassembly of any desired configuration adapted for mounting onto a device housing or the like, in combination with a feedthrough capacitor installed in operative relation with one or more terminal pins. In such embodiments, abrasive or microblast surface preparation of titanium materials may be desirable to remove surface oxides preparatory to the steps of welding, brazing, or application of conductive adhesives, etc., in order to obtain optimum electrical and hermetically sealed connections. In use, the feedthrough filter capacitor both suppresses and shields against undesired interference signals to prevent passage of those interference signals along the conductive lead pin 12, particularly in a heart pacemaker application or the like.

A variety of further modifications and improvements to the feedthrough filter capacitor assembly of the present invention will be apparent to those persons skilled in the art. Accordingly, no limitation on the invention is intended by way of the foregoing description and accompanying drawings, except as set forth in the appended claims.

What is claimed is:

1. A feedthrough filter capacitor assembly for use in an implantable medical device, said assembly comprising:
   at least one conductive terminal pin;
   means for mounting said terminal pin for passage through an opening formed in a conductive substrate with said terminal pin and substrate in nonconductive relation; and
   a feedthrough filter capacitor adapted for mounting axially at one outer side of said terminal pin mounting means and having a central opening formed therein for pass-through reception of said terminal pin;
   said capacitor having first and second sets of electrode plates adapted for electrical connection respectively to said terminal pin and substrate.

2. The feedthrough filter capacitor assembly of claim 1 wherein said filter capacitor comprises a discoidal capacitor.

3. The feedthrough filter capacitor of claim 2 wherein said discoidal capacitor has a radially open vent formed therein.

4. The feedthrough filter capacitor of claim 1 wherein said terminal pin mounting means includes means for hermetically sealing passage of said terminal pin through said substrate opening.

5. The feedthrough capacitor assembly of claim 1 wherein said terminal pin mounting means comprises a conductive ferrule adapted for mounting onto the substrate in a position extending through the substrate opening, and insulator means for supporting said terminal pin from said ferrule in electrically insulated relation.

6. The feedthrough filter capacitor assembly of claim 5 wherein said terminal pin, ferrule and insulator means comprises a prefabricated terminal pin subassembly.

7. The feedthrough filter capacitor assembly of claim 1 wherein said feedthrough filter capacitor is mounted onto the substrate.

8. The feedthrough filter capacitor assembly of claim 7 wherein said substrate comprises a subplate adapted for mounting onto a housing of the medical device.

9. The feedthrough filter capacitor assembly of claim 1 wherein said terminal pin mounting means includes a conductive ferrule adapted for mounting onto the substrate in a position extending through the substrate opening, said feedthrough filter capacitor being mounted onto said ferrule.

10. The feedthrough filter capacitor assembly of claim 1 wherein said capacitor has a recess formed at one side thereof for receiving at least a portion of said terminal pin mounting means whereby said capacitor circumferentially surrounds at least a portion of said terminal pin mounting means.

11. The feedthrough filter capacitor assembly of claim 10 wherein said filter capacitor comprises a base structure having said first and second sets of electrode plates embedded therein and further having said central opening formed therein, and a mounting ring mounted on said base structure at one side thereof, said base structure and said mounting ring cooperatively defining said recess.

12. The feedthrough filter capacitor assembly of claim 1 further including first means for electrically connecting said first set of electrode plates to said terminal pin, and second means for electrically connecting said second set of electrode plates to the substrate.

13. The feedthrough filter capacitor assembly of claim 12 wherein said first means and said second means comprise a conductive adhesive.

14. A feedthrough filter capacitor assembly for use in an implantable medical device, said assembly, comprising:
   a conductive substrate having an opening formed therein;
   a terminal pin subassembly including at least one elongated conductive terminal pin, a cylindrical conductive ferrule, and insulator means for mounting said terminal pin to extend through said ferrule in hermetically sealed, electrically insulated relation therewith;
   means for mounting said terminal pin subassembly onto said substrate with said terminal pin extending through the substrate opening and with said ferrule projecting generally coaxially with said substrate opening;
   a feedthrough filter capacitor including a dielectric base having at least one central opening formed therein; said dielectric base having embedded therein a first set of electrode plates each having a marginal edge exposed within said central opening, and a second set of electrode plates each having a marginal edge exposed at a selected outer surface of said base at a position remote from said central opening; and means for mounting said filter capacitor at one side of said substrate and axially at one outer side of said terminal pin mounting means, with said first and second sets of electrode plate electrically connected respectively to said terminal pin and said substrate.

15. The feedthrough filter capacitor assembly of claim 14 wherein said filter capacitor mounting means comprises a conductive adhesive.

16. The feedthrough filter capacitor assembly of claim 14 wherein said feedthrough filter capacitor is mounted onto the substrate.

17. The feedthrough filter capacitor assembly of claim 14 wherein said capacitor is mounted onto said ferrule.

18. The feedthrough filter capacitor assembly of claim 14 wherein said capacitor has a recess formed at one side thereof for receiving at least a portion of said terminal pin mounting means whereby said capacitor circumferentially surrounds at least a portion of said terminal pin mounting means.

19. A method of mounting a feedthrough filter capacitor to a conductive substrate, for use in an implantable medical device, said method comprising the steps of:

forming a terminal pin subassembly, including at least one elongated conductive terminal pin, a cylindrical conductive ferrule, and insulator means for mounting said terminal pin to extend through said ferrule in hermetically sealed, electrically insulated relation therewith;

mounting the terminal pin subassembly onto a conductive substrate with the terminal pin extending through a substrate opening and with said ferrule projecting generally coaxially with said substrate opening;

forming a feedthrough filter capacitor including a dielectric base having at least one central opening formed therein, said dielectric base having embedded therein a first set of electrode plates each having a marginal edge exposed within said central opening, and a second set of electrode plates each having a marginal edge exposed at a selected outer surface of said base at a position remote from said central opening; and mounting said filter capacitor onto a selected one of said substrate and said ferrule at one side of said substrate and axially at one side of the terminal pin subassembly, with said first and second sets of electrode plates electrically connected respectively to said terminal pin and said substrate.

20. A method of mounting a plurality of feedthrough filter capacitors to a conductive substrate for use in an implantable medical device, said method comprising the steps of:

forming a plurality of terminal pin subassemblies each including an elongated conductive terminal pin, a cylindrical conductive ferrule, and insulator means for mounting said terminal pin to extend through said ferrule in hermetically sealed, electrically insulated relation therewith;

mounting the terminal pin assemblies onto the substrate with the terminal pins extending respectively through the substrate in hermetically sealed, electrically insulated relation therewith;

forming a plurality of filter capacitors each including a dielectric base having a central opening formed therein, said dielectric base having embedded therein a first set of electrode plates each having a marginal edge exposed at a selected outer surface of said base at a position remote from said central opening, and wherein the base of each of said capacitors comprises a unitary base structure; and mounting said unitary base structure onto a selected one of the substrate and ferrule axially at one side of the terminal pin subassemblies, with said first and second electrode sets of each of said capacitors electrically connected respectively to the associated one of the terminal pins and to the substrate.

21. A method of mounting a feedthrough filter capacitor to a conductive substrate, for use in an implantable medical device, said method comprising the steps of:

forming a terminal pin subassembly, including at least one elongated conductive terminal pin, a cylindrical conductive ferrule, and insulator means for mounting said terminal pin to extend through said ferrule in heremetically sealed, electrically insulated relation therewith;

forming a feedthrough filter capacitor including a dielectric base having at least one central opening formed therein, said dielectric base having embedded therein a first set of electrode plates each having a marginal edge exposed within said central opening, and a second set of electrode plates each having a marginal edge exposed at a selected outer surface of said base at a position remote from said central opening;

mounting said filter capacitor axially at one outer side of said ferrule with said first and second sets of electrode plates electrically connected respectively to said terminal pin and said ferrule; and thereafter mounting the terminal pin subassembly onto the conductive substrate with the terminal pin extending through a substrate opening and with said ferrule projecting generally coaxially with said substrate opening.

* * * * *